United States Patent
Gomi et al.

(10) Patent No.: US 9,352,574 B2
(45) Date of Patent: May 31, 2016

(54) FLUID EJECTION DEVICE

(71) Applicant: SEIKO EPSON CORPORATION, Tokyo (JP)

(72) Inventors: Masaki Gomi, Hino (JP); Kazuaki Uchida, Fujimi-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/683,035

(22) Filed: Apr. 9, 2015

(65) Prior Publication Data
US 2015/0290944 A1 Oct. 15, 2015

(30) Foreign Application Priority Data
Apr. 10, 2014 (JP) ................................. 2014-080829

(51) Int. Cl.
*B41J 29/393* (2006.01)
*B41J 2/175* (2006.01)
*B41J 29/38* (2006.01)

(52) U.S. Cl.
CPC .............. *B41J 2/175* (2013.01); *B41J 2/17556* (2013.01); *B41J 2/17596* (2013.01); *B41J 29/38* (2013.01)

(58) Field of Classification Search
CPC .. A61B 17/3203; B41J 2/175; B41J 2/17556; B41J 2/17596; B41J 29/38; B41J 29/393
See application file for complete search history.

(56) References Cited

U.S. PATENT DOCUMENTS

| | | | | |
|---|---|---|---|---|
| 5,259,842 A | * | 11/1993 | Plechinger et al. | 604/152 |
| 5,505,729 A | * | 4/1996 | Rau | 606/40 |
| 5,871,462 A | * | 2/1999 | Yoder et al. | 604/22 |
| 2008/0007579 A1 | * | 1/2008 | Furukawa et al. | 347/6 |
| 2009/0043480 A1 | * | 2/2009 | Seto et al. | 701/103 |
| 2009/0314314 A1 | * | 12/2009 | Klein et al. | 134/32 |
| 2010/0078495 A1 | * | 4/2010 | Seto et al. | 239/1 |
| 2011/0036859 A1 | * | 2/2011 | Matsuzaki et al. | 222/1 |
| 2011/0054505 A1 | * | 3/2011 | Kojima et al. | 606/167 |
| 2011/0194945 A1 | * | 8/2011 | Kensy et al. | 417/26 |
| 2011/0208224 A1 | * | 8/2011 | Kojima | 606/167 |
| 2012/0176431 A1 | * | 7/2012 | Kojima | 347/14 |
| 2013/0158544 A1 | * | 6/2013 | Kuhner et al. | 606/39 |
| 2014/0296892 A1 | * | 10/2014 | Uchida et al. | 606/167 |

FOREIGN PATENT DOCUMENTS

JP 2013-213422 A 10/2013

* cited by examiner

*Primary Examiner* — Julian Huffman
(74) *Attorney, Agent, or Firm* — Maschoff Brennan

(57) ABSTRACT

A fluid ejection device includes a fluid container having a fluid accommodation portion that has formed therein a fluid outlet and accommodates a fluid. A fluid pressing unit presses the fluid accommodation portion to cause the fluid to flow out of the fluid outlet. Connection piping has an end that is connected to the fluid outlet. A fluid ejection unit has a fluid intake port connected to the other end of the connection piping, and ejects in a pulsed manner the fluid received from the fluid intake port. A pressure detection unit detects pressure of the fluid accommodation portion when the fluid pressing unit presses the fluid accommodation portion, and outputs a level of a detection signal corresponding to the pressure. A press control unit stops the fluid pressing unit from pressing the fluid accommodation portion when the pressure indicated by the detection signal is a predetermined value or higher.

10 Claims, 7 Drawing Sheets

FLUID EJECTION DEVICE

This application claims the benefit of Japanese Patent Application No. 2014-080829 filed, on Apr. 10, 2014. The content of the aforementioned application is incorporated herein by reference in its entirety.

BACKGROUND

1. Technical Field

The present invention relates to a fluid ejection device.

2. Related Art

A technology in which an object is incised or excised by ejecting a pulsed fluid is known. For example, in the medical field, a fluid ejection device is proposed as an operation scalpel to incise or excise living tissue, the fluid ejection device being configured to include a pulsation generator that ejects a pulsed fluid, a fluid supply unit that supplies a fluid to the pulsation generator, a fluid supply path configured from the fluid supply unit to the pulsation generator, and an operation switch that switches between an ejection mode and a non-ejection mode (refer to JP-A-2013-213422).

In the device, it is necessary to maintain the fluid in the fluid supply path at a proper pressure so as to continuously and stably eject the fluid from the pulsation generator. For this reason, when the pulsation generator ejects the fluid corresponding to an input state of the operation switch, the fluid supply unit performs a control operation in such a manner that a corresponding amount of the fluid is supplied to the fluid supply path.

Accordingly, in a state where the fluid supply path is blocked for unknown reasons, and when the fluid is continuously supplied from the fluid supply unit to the fluid supply path, an inner pressure in the fluid supply path increases. As a result, a malfunction such as a leakage of the fluid or a failure of the fluid ejection device may occur.

SUMMARY

An advantage of some aspects of the invention is to provide a technology in which it is possible to improve the safety or the reliability of a fluid ejection device by detecting the blocking of the fluid supply path.

A fluid ejection device according to an aspect of the invention includes: a fluid container that has a fluid accommodation portion for accommodating a fluid, and a fluid outlet formed in the fluid accommodation portion; a fluid pressing unit that presses the fluid accommodation portion to cause the fluid to flow out of the fluid outlet; connection piping, one end of which is connected to the fluid outlet; a fluid ejection unit that has a fluid intake port connected to the other end of the connection piping, and ejects in a pulsed manner the fluid taken in via the fluid intake port; a pressure detection unit that detects a pressure of the fluid accommodation portion when the fluid pressing unit presses the fluid accommodation portion, and outputs a detection signal corresponding to the pressure; and a press control unit that stops the fluid pressing unit from pressing the fluid accommodation portion when the pressure indicated by the detection signal is a predetermined determination value or higher.

Other features of the invention will be made apparent by the description of this specification and the accompanying drawings.

BRIEF DESCRIPTION OF THE DRAWINGS

The invention will be described with reference to the accompanying drawings, wherein like numbers reference like elements.

DESCRIPTION OF EXEMPLARY EMBODIMENTS

Outline

Figure 1:
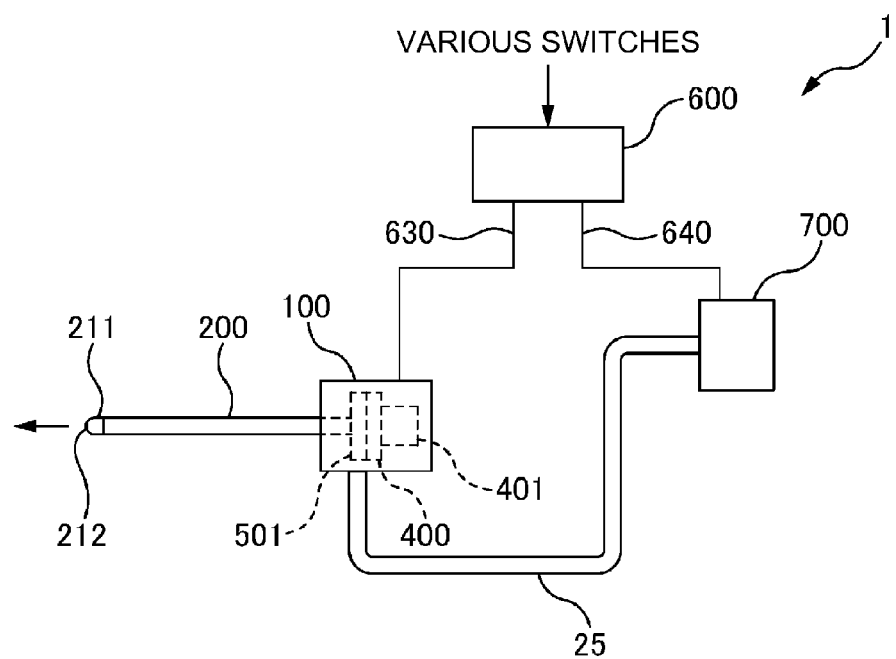
FIG. 1 is a block diagram illustrating an example of the entire configuration of a fluid ejection device according to an embodiment of the invention.

At least the following facts are apparent from this specification and the accompanying drawings.

A fluid ejection device includes: a fluid container that has a fluid accommodation portion for accommodating a fluid, and a fluid outlet formed in the fluid accommodation portion; a fluid pressing unit that presses the fluid accommodation portion to cause the fluid to flow out of the fluid outlet; connection piping, one end of which is connected to the fluid outlet; a fluid ejection unit that has a fluid intake port connected to the other end of the connection piping, and ejects in a pulsed manner the fluid taken in via the fluid intake port; a pressure detection unit that detects a pressure of the fluid accommodation portion when the fluid pressing unit presses the fluid accommodation portion, and outputs a detection signal corresponding to the pressure; and a press control unit that stops the fluid pressing unit from pressing the fluid accommodation portion when the pressure indicated by the detection signal is a predetermined determination value or higher.

In the fluid ejection device, it is possible to detect the blocking of the connection piping that acts as the fluid channel between the fluid pressing unit and the fluid ejection unit, and to improve the safety or the reliability of the fluid ejection device.

In the fluid ejection device, it is preferable that the press control unit stops the pressing of the fluid accommodation portion by shutting off electrical power used when the fluid pressing unit presses the fluid accommodation portion.

In the fluid ejection device, it is possible to reliably stop the pressing of the fluid accommodation portion.

In the fluid ejection device, it is preferable that, when the pressure indicated by the detection signal is the predetermined determination value or higher, the press control unit stops the fluid pressing unit from pressing the fluid accommodation portion, and stops the fluid ejection unit from ejecting the fluid in a pulsed manner.

In the fluid ejection device, since it is possible to prevent residual pressure in the connection piping from causing the fluid ejection unit to continuously eject the fluid at a high pressure, it is possible to further improve the safety of the fluid ejection device.

In the fluid ejection device, it is preferable that the predetermined determination value is a value determined corresponding to a target pressure value when the fluid pressing unit presses the fluid accommodation portion.

As such, even though the target pressure value is changed according to circumstances from moment to moment, it is possible to properly detect the blocking of the connection piping by detecting the blocking of the connection piping using the determination value determined corresponding to the target pressure value.

It is preferable that the fluid ejection device further includes: an operation input unit that receives an operation input to enable or disable the ejection of the fluid from the fluid ejection unit; and a drive control unit that drives a pressurization element provided in the fluid ejection unit so as to apply a pulsed pressure to the fluid taken in via the fluid intake port when the drive control unit receives an operation input to enable the ejection of the fluid, and stops the driving of the pressurization element when the drive control unit receives an operation input to disable the ejection of the fluid, and when the pressurization element is being driven, the press control unit compares the pressure indicated by the detection signal with a first determination value determined corresponding to the target pressure value when the fluid pressing unit presses the fluid accommodation portion, and when the pressurization element is not being driven, the press control unit compares the pressure indicated by the detection signal with a second determination value that is a predetermined fixed value.

In the fluid ejection device, when the fluid is being ejected from the fluid ejection unit, it is possible to precisely detect the blocking of the connection piping by detecting the blocking of the connection piping by using the determination value (the first determination value) determined corresponding to the target pressure value when the fluid pressing unit presses the fluid accommodation portion, and when the fluid is not being ejected, in which there is no target pressure value set, it is possible to detect the blocking of the connection piping by using the determination value (the second determination value) that is the predetermined fixed value.

In the fluid ejection device, it is preferable that, when the pressure indicated by the detection signal is the determination value or higher, the press control unit outputs an alarm to notify that the pressure is the determination value or higher.

In the fluid ejection device, it is possible to promptly notify an operator such as a practitioner that the connection piping is blocked, and it is possible to further improve the safety of the fluid ejection device.

In the fluid ejection device, it is preferable that, when the pressure indicated by the detection signal is the determination value or higher, the press control unit stops the fluid pressing unit from pressing the fluid accommodation portion, and reduces an inner pressure of the fluid accommodation portion.

In the fluid ejection device, since it is possible to rapidly release a high pressure originating from the blocking of the connection piping, and to easily reduce the high pressure to a safe level, it is possible to further improve the safety of the fluid ejection device. In addition, thereafter, it is possible to more safely perform maintenance or the like.

In the fluid ejection device, it is preferable that the press control unit includes an AD converter that receives the detection signal from the pressure detection unit, and outputs detected level data indicative of the level of the detection signal, a memory that stores determination value level data indicative of the level of the determination value, a processor that outputs a first stop signal for stopping the fluid pressing unit from pressing the fluid accommodation portion to the fluid pressing unit when the detected level data from the AD converter is compared with the determination value level data stored in the memory, and the detected level data is the determination value level data or greater, a determination value signal output circuit that outputs a level of a determination value signal equivalent to the determination value, a comparator circuit that outputs a second stop signal for stopping the fluid pressing unit from pressing the fluid accommodation portion when the detection signal from the pressure detection unit and the determination value signal are input to the comparator circuit, the level of the detection signal is compared with the level of the determination value signal, and the level of the detection signal is the level of the determination value signal or higher, and a latch circuit that receives the second stop signal from the comparator circuit, and outputs the second stop signal to the fluid pressing unit at a timing synchronous with a predetermined frequency of a clock signal, and when the first stop signal or the second stop signal is input, the fluid pressing unit stops the pressing of the fluid accommodation portion, and the processor outputs a reset signal to the latch circuit so as to reset the latch circuit before the latch circuit outputs the second stop signal synchronously with the clock signal.

The fluid ejection device can detect the blocking of the connection piping without the processor being intervened. For this reason, for example, even when a failure of the processor occurs, it is possible to prevent occurrences of various malfunctions associated with the blocking of the connection piping. Accordingly, it is possible to further improve the safety or the reliability of the fluid ejection device.

On the other hand, in a case where the processor operates normally, and even when the level of the detection signal from the pressure detection unit increases temporarily due to noise or the like, the processor resets the latch circuit before the second stop signal is output to the fluid pressing unit from the latch circuit, and thereby it is possible to prevent the fluid pressing unit from erroneously being stopped. Accordingly, it is possible to improve the reliability of the fluid ejection device.

Entire Configuration

Hereinafter, an embodiment of the invention will be described with reference to the accompanying drawings. A fluid ejection device according to the embodiment can be used in various procedures such as the cleaning or cutting of a fine object or structure, living tissue, or the like; however, an example of the embodiment given in the following description is the fluid ejection device suitable for use as an operation scalpel to incise or excise living tissue. Accordingly, a fluid used in the fluid ejecting device according to the embodiment is water, physiologic saline, a predetermined fluid medicine, or the like. The drawings referenced in the following description are schematic views in which a member or a portion is vertically and horizontally scaled differently from an actual scale for illustrative purposes.

FIG. 1 is a view illustrating the configuration of a fluid ejection device 1 as an operation scalpel according to the embodiment. The fluid ejection device 1 according to the embodiment includes: a pump 700 for supplying a fluid; a pulsation generator (a fluid ejection unit) 100 that converts a flow of the fluid supplied from the pump 700 into a pulsed flow, and ejects the fluid in a pulsed manner; a drive control unit 600 that controls the fluid ejection device 1 in cooperation with the pump 700; and a connection tube 25 as a connection path (connection piping) acting as a channel through which the pump 700 and the pulsation generator 100 is connected to each other, and the fluid flows.

The pulsation generator 100 includes: a fluid chamber 501 that accommodates the fluid supplied from the pump 700; a diaphragm 400 that changes the volume of the fluid chamber 501; and a piezoelectric element (a pressurization element) 401 that vibrates the diaphragm 400, all of which will be described later in detail.

The pulsation generator 100 includes a thin pipe-like fluid ejection tube 200 that acts as a channel of the fluid discharged from the fluid chamber 501, and a nozzle 211 that is mounted on a tip end portion of the fluid ejection tube 200 and has a reduced channel diameter.

The pulsation generator 100 converts a flow of the fluid into a pulsed flow by applying a pulsed pressure to the fluid via the driving of the piezoelectric element 401 in response to drive signals output from the drive control unit 600 and the changing of the volume of the fluid chamber 501, and the pulsation generator 100 ejects at a high speed the fluid in a pulsed manner via the fluid ejection tube 200 and the nozzle 211.

The drive control unit 600 and the pulsation generator 100 are connected to each other via a control cable 630, and drive signals for driving the piezoelectric element 401 are output from the drive control unit 600, and are transmitted to the pulsation generator 100 via the control cable 630.

The drive control unit 600 and the pump 700 are connected to each other via a communication cable 640, and the drive control unit 600 and the pump 700 transmit and receive various commands or data therebetween according to a predetermined communication protocol such as a controller area network (CAN).

The drive control unit 600 receives signals from various switches operated by a practitioner who performs an operation using the pulsation generator 100, and controls the pump 700 or the pulsation generator 100 via the control cable 630 or the communication cable 640.

The switches that input signals to the drive control unit 600 are a pulsation generator start-up switch (an operation input unit) 625, an ejection intensity switching switch 627, a flushing switch 628, and the like (not illustrated).

The pulsation generator start-up switch 625 is a switch for switching between the ejection and the non-ejection of the fluid from the pulsation generator 100 (the turning on and off of the pulsation generator 100). When a practitioner who performs an operation using the pulsation generator 100 operates the pulsation generator start-up switch 625, the drive control unit 600 controls the pulsation generator 100 to eject the fluid or stop the ejection of the fluid in cooperation with the pump 700. The pulsation generator start-up switch 625 can be a foot switch configured to be operated by the practitioner's foot, or a switch that is provided integrally with the pulsation generator 100 grasped by the practitioner, and configured to be operated by the practitioner's hands or fingers.

The ejection intensity switching switch 627 is a switch for changing the intensity of fluid ejection from the pulsation generator 100. When the ejection intensity switching switch 627 is operated, the drive control unit 600 controls the pulsation generator 100 and the pump 700 so as to increase and decrease the intensity of fluid ejection.

The flushing switch 628 will be described later.

In the embodiment, a pulsed flow implies a flow of a fluid, a flow direction of which is constant, and the flow rate or flow speed of which is changed periodically or non-periodically. The pulsed flow may be an intermittent flow in which the flowing and stopping of the fluid are repeated; however, since the flow rate or flow speed of the fluid is preferably changed periodically or non-periodically, the pulsed flow is not necessarily an intermittent flow.

Similarly, the ejection of a fluid in a pulsed form implies the ejection of the fluid by which the flow rate or moving speed of an ejected fluid is changed periodically or non-periodically. An example of the pulsed ejection is an intermittent ejection by which the ejection and non-ejection of a fluid are repeated; however, since the flow rate or moving speed of an ejected fluid is preferably changed periodically or non-periodically, the pulsed ejection is not necessarily an intermittent ejection.

When the driving of the pulsation generator 100 is stopped, that is, when the volume of the fluid chamber 501 is not changed, the fluid supplied from the pump 700 as a fluid supply unit at a predetermined pressure continuously flows out of the nozzle 211 via the fluid chamber 501.

Figure 2:
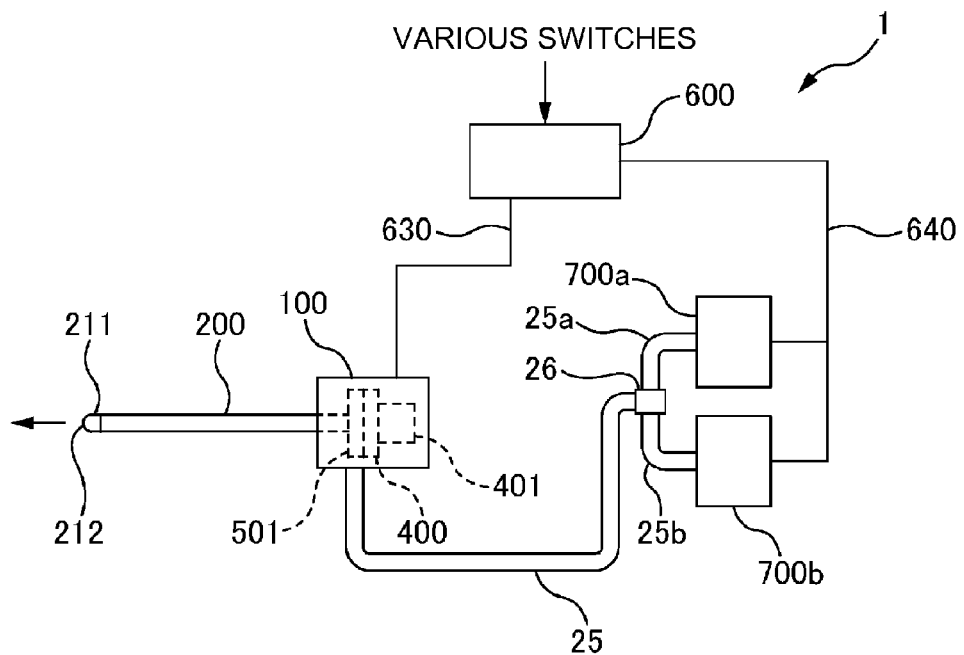
FIG. 2 is a block diagram illustrating another example of the entire configuration of the fluid ejection device according to the embodiment of the invention.

The fluid ejection device 1 according to the embodiment may be configured to include a plurality of the pumps 700. FIG. 2 illustrates an example of the configuration of the fluid ejection device 1 configured to include two pumps 700.

In this case, as illustrated in FIG. 2, the fluid ejection device 1 includes a first pump 700a and a second pump 700b. A first connection tube 25a, a second connection tube 25b, a connection tube 25, and a three way stopcock 26 form the connection path (connection piping) which connects the pulsation generator 100 and the first pump 700a, and the pulsation generator 100 and the second pump 700b, and acts as a channel through which the fluid flows.

The three way stopcock 26 is a valve configured to be able to communicate the first connection tube 25a and the connection tube 25, or the second connection tube 25b and the connection tube 25, and either one of the first pump 700a and the second pump 700b is selectively used.

In this configuration, for example, when the first pump 700a cannot supply the fluid for unknown reasons such as a malfunction while being selected and used, it is possible to continuously use the fluid ejection device 1 and to minimize adverse effects associated with the non-supply of the fluid from the first pump 700a by switching the three way stopcock 26 so as to communicate the second connection tube 25b and the connection tube 25, and starting the supply of the fluid from the second pump 700b.

When the fluid ejection device 1 is configured to include a plurality of the pumps 700, but the pumps 700 are not required to be distinctively described, in the following description, the pumps 700 are collectively expressed by the pump 700.

In contrast, when the plurality of pumps 700 are required to be distinctively described, suffixes such as "a" and "b" are properly added to reference sign 700 of the pump, and each of the pumps 700 is distinctively expressed by the first pump 700a or the second pump 700b. In this case, each configuration element of the first pump 700a is expressed by adding the suffix "a" to a reference sign of each configuration element, and each configuration element of the second pump 700b is expressed by adding the suffix "b" to a reference sign of each configuration element.

Pump

Subsequently, an outline of the configuration and operation of the pump 700 according to the embodiment will be described with reference to FIG. 3.

The pump 700 according to the embodiment includes a pump control unit (a press control unit) 710; a slider 720; a motor 730; a linear guide 740; and a pinch valve 750. The pump 700 is configured to have a fluid container mounting unit 770 for attachably and detachably mounting a fluid container 760 that accommodates the fluid. The fluid container mounting unit 770 is formed so as to hold the fluid container 760 at a specific position when the fluid container 760 is mounted thereon.

The following switches (which will be described later in detail) (not illustrated) are connected to the pump control unit 710: a slider release switch 780; a slider set switch 781; a fluid supply ready switch 782; a priming switch 783; and a pinch valve switch 785.

In the embodiment, for example, the fluid container 760 is formed of a medical syringe configured to include a syringe 761 and a plunger 762.

In the fluid container 760, a protrusive cylinder-shaped opening (an fluid outlet) 764 is formed in a tip end portion of the syringe 761. When the fluid container 760 is mounted on the fluid container mounting unit 770, an end portion of the connection tube 25 is inserted into the opening 764, and a fluid channel is formed from the inside of the syringe 761 to the connection tube 25.

The pinch valve 750 is a valve that is provided on a path of the connection tube 25, and opens and closes a fluid channel between the fluid container 760 and the pulsation generator 100.

The pump control unit 710 controls the opening and closing of the pinch valve 750. When the pump control unit 710 opens the pinch valve 750, the fluid container 760 and the pulsation generator 100 communicate with each other via the channel therebetween. When the pump control unit 710 closes the pinch valve 750, the channel between the fluid container 760 and the pulsation generator 100 is shut off.

In a state where the fluid container 760 is mounted on the fluid container mounting unit 770, and the pinch valve 750 is opened, when the plunger 762 of the fluid container 760 moves in a direction (hereinafter, also referred to as a push-in direction) in which the plunger 762 is pushed into the syringe 761, the volume of a space (hereinafter, also referred to as a fluid accommodation portion 765) is reduced, the space being enveloped by an end surface of a gasket 763 made of resin such as elastic rubber and mounted at the tip of the plunger 762 in the push-in direction, and an inner wall of the syringe 761, and the fluid in the fluid accommodation portion 765 is discharged via the opening 764 of the tip end portion of the syringe 761. The connection tube 25 is filled with the fluid discharged via the opening 764, and the discharged fluid is supplied to the pulsation generator 100.

In contrast, in a state where the fluid container 760 is mounted on the fluid container mounting unit 770, and the pinch valve 750 is closed, when the plunger 762 of the fluid container 760 moves in the push-in direction, it is possible to reduce the volume of the fluid accommodation portion 765, the fluid accommodating portion 765 being enveloped by the gasket 763 mounted at the tip of the plunger 762 and the inner wall of the syringe 761, and it is possible to increase the pressure of the fluid in the fluid accommodation portion 765.

The pump control unit 710 moves the slider 720 along a direction (in the push-in direction and the opposite direction of the push-in direction) in which the plunger 762 slides in a state where the fluid container 760 is mounted on the fluid container mounting unit 770, and the plunger 762 moves in accordance with the movement of the slider 720.

Specifically, the slider 720 is attached to the linear guide 740 in such a manner that a pedestal 721 of the slider 720 engages with a rail (not illustrated) formed linearly on the linear guide 740 along the slide direction of the plunger 762. The linear guide 740 moves the pedestal 721 of the slider 720 along the rail using power transmitted from the motor 730 driven by the pump control unit 710, and thereby the slider 720 moves along the slide direction of the plunger 762.

Figure 3:
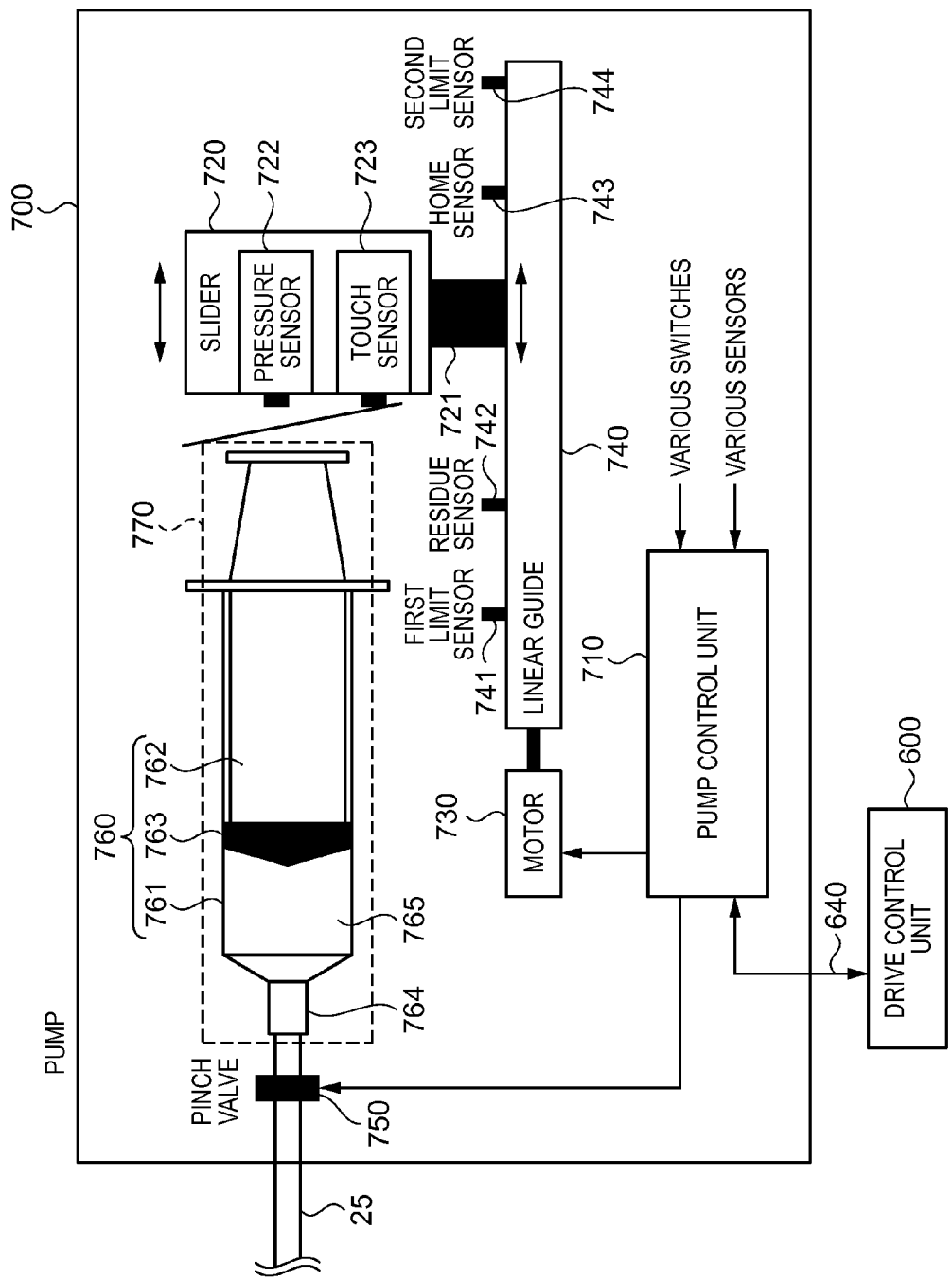
FIG. 3 is a block diagram illustrating the configuration of a pump according to the embodiment of the invention.

As illustrated in FIG. 3, the following sensors are provided along the rail of the linear guide 740: a first limit sensor 741; a residue sensor 742; a home sensor 743; and a second limit sensor 744.

All of the first limit sensor 741, the residue sensor 742, the home sensor 743, and the second limit sensor 744 are sensors for detecting the position of the slider 720 that moves on the rail of the linear guide 740, and signals detected by these sensors are input to the pump control unit 710.

The home sensor 743 is a sensor used to determine an initial position (hereinafter, also referred to as a home position) of the slider 720 on the linear guide 740. The home position is a position in which the slider 720 is held when the fluid container 760 is mounted or replaced.

The residue sensor 742 is a sensor for detecting the position (hereinafter, also referred to as a residual position) of the slider 720 when the residue of the fluid in the fluid container 760 is less than or equal to a predetermined value while the slider 720 moves from the home position in the push-in direction of the plunger 762. When the slider 720 reaches the residual position in which the residue sensor 742 is provided, a predetermined alarm is output to an operator (a practitioner or an assistant). The fluid container 760 currently in use is replaced with a new fluid container 760 at an appropriate time determined by the operator. Alternatively, when the auxiliary second pump 700b having the same configuration as that of the pump 700 (the first pump 700a) is prepared, a switching operation is performed so as to supply the fluid from the auxiliary second pump 700b to the pulsation generator 100.

The first limit sensor 741 indicates a limit position (hereinafter, referred to as a first limit position) in a movable range in which the slider 720 can move from the home position in the push-in direction of the plunger 762. When the slider 720 reaches the first limit position in which the first limit sensor 741 is provided, the residue of the fluid in the fluid container 760 is much less than the residue indicating that the slider 720 is present at the residual position, and a predetermined alarm is output to the operator. In this case, the fluid container 760 currently in use is also replaced with a new fluid container 760, or a switching operation is also performed so as to supply the fluid from an auxiliary second pump 700b.

In contrast, the second limit sensor 744 indicates a limit position (hereinafter, also referred to as a second limit position) in a movable range in which the slider 720 can move from the home position in the opposite direction of the push-in direction of the plunger 762. When the slider 720 reaches the second limit position in which the second limit sensor 744 is provided, a predetermined alarm is output.

A touch sensor 723 and a pressure sensor (a pressure detection unit) 722 are mounted on the slider 720.

The touch sensor 723 is a sensor for detecting whether the slider 720 is in contact with the plunger 762 of the fluid container 760.

The pressure sensor 722 is a sensor that detects the pressure of the fluid in the fluid accommodation portion 765 formed by the inner wall of the syringe 761 and the gasket 763, that is, a pressure when the slider 720 presses the fluid accommodation portion 765, and outputs signals (detection signals) at a level (for example, a voltage, or a voltage and a frequency) that corresponds to a detected pressure.

When the pinch valve 750 is closed, and the slider 720 moves in the push-in direction, and after the slider 720 comes into contact with the plunger 762, the pressure of the fluid in the fluid accommodation portion 765 increases to the extent that the slider 720 moves further in the push-in direction.

In contrast, when the pinch valve 750 is opened, and the slider 720 moves in the push-in direction, and even after the slider 720 comes into contact with the plunger 762, the fluid in the fluid accommodation portion 765 flows out of the nozzle 211 of the pulsation generator 100 via the connection tube 25, and thereby the pressure of the fluid in the fluid accommodation portion 765 increases to a certain level, but the pressure of the fluid does not increase even though the slider 720 moves further in the push-in direction.

The touch sensor 723 and the pressure sensor 722 input signals to the pump control unit 710.

In the following description, the slider 720, the motor 730, and the linear guide 740 may be referred to as a fluid pressing unit 731. The fluid pressing unit 731 causes the fluid to flow out of the opening (the fluid outlet) 764 of the fluid container 760 by pressing the fluid accommodation portion 765.

A description to be given hereinafter is regarding a preparation operation configured to include a process of mounting a fluid container 760 filled with the fluid on the fluid container mounting unit 770; a process of supplying the fluid in the fluid container 760 to the pulsation generator 100; and a process of bringing the fluid ejection device 1 into a state in which the pulsation generator 100 can eject the fluid in the form of a pulsed flow.

First, the operator inputs an ON signal of the slider release switch 780 to the pump control unit 710 by operating the slider release switch 780. Thus, the pump control unit 710 moves the slider 720 to the home position.

The operator mounts the fluid container 760 connected to the connection tube 25 in advance on the fluid container mounting unit 770. The syringe 761 of the fluid container 760 is already filled with the fluid.

When the operator sets the connection tube 25 to the pinch valve 750, and then inputs an ON signal of the pinch valve switch 785 to the pump control unit 710 by operating the pinch valve switch 785, the pump control unit 710 closes the pinch valve 750.

Subsequently, the operator inputs an ON signal of the slider set switch 781 to the pump control unit 710 by operating the slider set switch 781. Thus, the pump control unit 710 starts a control operation in such a manner that the slider 720 moves in the push-in direction and the pressure of the fluid accommodated in the fluid accommodation portion 765 of the fluid container 760 becomes a predetermined target pressure value.

Thereafter, when the operator inputs an ON signal of the fluid supply ready switch 782 to the pump control unit 710 by pushing the fluid supply ready switch 782, and the pressure of the fluid in the fluid container 765 enters a specific range (hereinafter, also referred to as a rough window) for the target pressure value, the pump control unit 710 is brought into a fluid suppliable state in which the fluid is allowed to be supplied from the pump 700 to the pulsation generator 100.

When the pump control unit 710 is in a fluid suppliable state, and the operator inputs an ON signal of the priming switch 783 to the pump control unit 710 by operating the priming switch 783, the pump control unit 710 starts a priming process. The priming process is a process by which a fluid channel from the fluid container 760 to the connection tube 25 and to a fluid ejection opening 212 of the pulsation generator 100 is filled up with the fluid.

When the priming process starts, the pump control unit 710 opens the pinch valve 750, and starts moving the slider 720 in the push-in direction at the same time or substantially the same time (for example, a time gap of approximately several milliseconds) as when the pinch valve 750 is opened. The slider 720 moves at a predetermined speed in such a manner that a constant amount of the fluid per unit time is supplied from the fluid container 760. The priming process is performed until a predetermined amount of time required to complete the priming process has elapsed (or the slider 720 moves by a predetermined distance), or the operator inputs an OFF signal of the priming switch 783 by operating the priming switch 783.

Accordingly, a predetermined amount of the fluid in the fluid container 765 is supplied at a predetermined flow speed (the amount of discharge of the fluid per unit time) from the pump 700, the connection tube 25 from the pinch valve 750 to the pulsation generator 100 is filled up with the fluid, and the fluid chamber 501 of the pulsation generator 100, the fluid ejection tube 200 and the like are filled up with the fluid. Air present in the connection tube 25 or the pulsation generator 100 prior to the start of the priming process is released to the atmosphere via the nozzle 211 of the pulsation generator 100 as the fluid flows into the connection tube 25 or the pulsation generator 100.

The pump control unit 710 pre-stores the predetermined speed, the predetermined distance, and the predetermined amount of time in relation to the movement of the slider 720 during the priming process.

As such, the priming process is completed.

Subsequently, when the operator inputs an ON signal of the flushing switch 628 to the drive control unit 600 by operating the flushing switch 628, the drive control unit 600 and the pump control unit 710 start a deaeration process.

The deaeriation process is a process by which air bubbles remaining in the connection tube 25 or the pulsation generator 100 are discharged via the nozzle 211 of the pulsation generator 100.

In the deaeriation process, in a state in which the pinch valve 750 is opened, the pump control unit 710 moves the slider 720 in the push-in direction at the predetermined speed in such a manner that a constant amount of the fluid per unit time is supplied from the fluid container 760, and the fluid is supplied to the pulsation generator 100. The drive control unit 600 drives the piezoelectric element 401 of the pulsation generator 100 in conjunction with the discharge of the fluid by the pump 700, and thereby the pulsation generator 100 to eject the fluid. Accordingly, air bubbles remaining in the connection tube 25 or the pulsation generator 100 are discharged via the nozzle 211 of the pulsation generator 100. The deaeriation process is performed until a predetermined amount of time has elapsed (or the slider 720 moves by a predetermined distance), or the operator inputs an OFF signal of the flushing switch 628 by operating the flushing switch 628.

The drive control unit 600 and the pump control unit 710 pre-store the predetermined speed, the predetermined distance, and the predetermined amount of time in relation to the movement of the slider 720 during the deaeriation process.

When the deaeriation process is completed, the pump control unit 710 closes the pinch valve 750, and detects the pressure of the fluid accommodated in the fluid accommodation portion 765 of the fluid container 760. The pump control unit 710 performs a control operation in which the position of the slider 720 is adjusted in order for the pressure to become the target pressure value.

Thereafter, when the pressure of the fluid in the fluid container 765 enters a specific range (a rough window) for the target pressure value, the pump control unit 710 is brought into a fluid ejectable state in which the fluid can be ejected in the form of a pulsed flow from the pulsation generator 100.

In this state, when the operator inputs an ON signal of the pulsation generator start-up switch 625 to the drive control unit 600 by operating the pulsation generator start-up switch 625 by the foot, the pump control unit 710 opens the pinch valve 750 in response to signals transmitted from the drive control unit 600, and starts the supply of the fluid to the pulsation generator 100 by moving the slider 720 at a predetermined speed in the push-in direction at the same time or substantially the same time (for example, a time gap of approximately several milliseconds) as when the pinch valve 750 is opened. In contrast, the drive control unit 600 generates a pulsed flow by starting the driving of the piezoelectric element 401 and changing the volume of the fluid chamber 501. Accordingly, a pulsed flow of the fluid is ejected at a high speed via the nozzle 211 at the tip of the pulsation generator 100.

Thereafter, when the operator inputs an OFF signal of the pulsation generator start-up switch 625 to the drive control unit 600 by operating the pulsation generator start-up switch 625 by the foot, the drive control unit 600 stops the driving of the piezoelectric element 401. The pump control unit 710 stops the movement of the slider 720 in response to signals transmitted from the drive control unit 600, and closes the pinch valve 750. As such, the pulsation generator 100 stops the ejection of the fluid.

In the embodiment, the fluid container 760 is formed of a medical syringe configured to include a syringe 761 and a plunger 762; however, the fluid container 760 can be also configured differently. For example, the fluid container 760 may be an infusion solution bag that accommodates the fluid. In this case, the infusion solution bag as the fluid container 760 is mounted on the fluid container mounting unit 770. In a state where the connection tube 25 is connected to an opening in the infusion solution bag so as to take the fluid out of the infusion solution bag, and when the infusion solution bag is pressed by a mechanism that presses the perimeter of the infusion solution bag, the fluid is supplied to the pulsation generator 100 from the infusion solution bag in the pump 700.

In addition, in the embodiment, the drive control unit 600 is provided separately from the pump 700 and the pulsation generator 100; however, the drive control unit 600 may be provided integrally with the pump 700.

When the practitioner performs an operation using the fluid ejection device 1, the practitioner grasps the pulsation generator 100. Accordingly, the connection tube 25 up to the pulsation generator 100 is preferably as flexible as possible. For this reason, a flexible thin tube is used as the connection tube 25, and a fluid discharge pressure of the pump 700 is preferably set to a low pressure in a pressure range in which the fluid can be supplied to the pulsation generator 100. For this reason, the discharge pressure of the pump 700 is set to approximately 0.3 atm (0.03 MPa) or less.

In particular, in a case where a malfunction of an apparatus may lead to a serious accident, for example, for a brain surgery, it is necessary to prevent the cutting of the connection tube 25 from causing the ejection of the fluid at a high pressure, and also, for this reason, the discharge pressure of the pump 700 is required to be set to a low pressure.

Pulsation Generator

Subsequently, the structure of the pulsation generator 100 according to the embodiment will be described.

Figure 4:
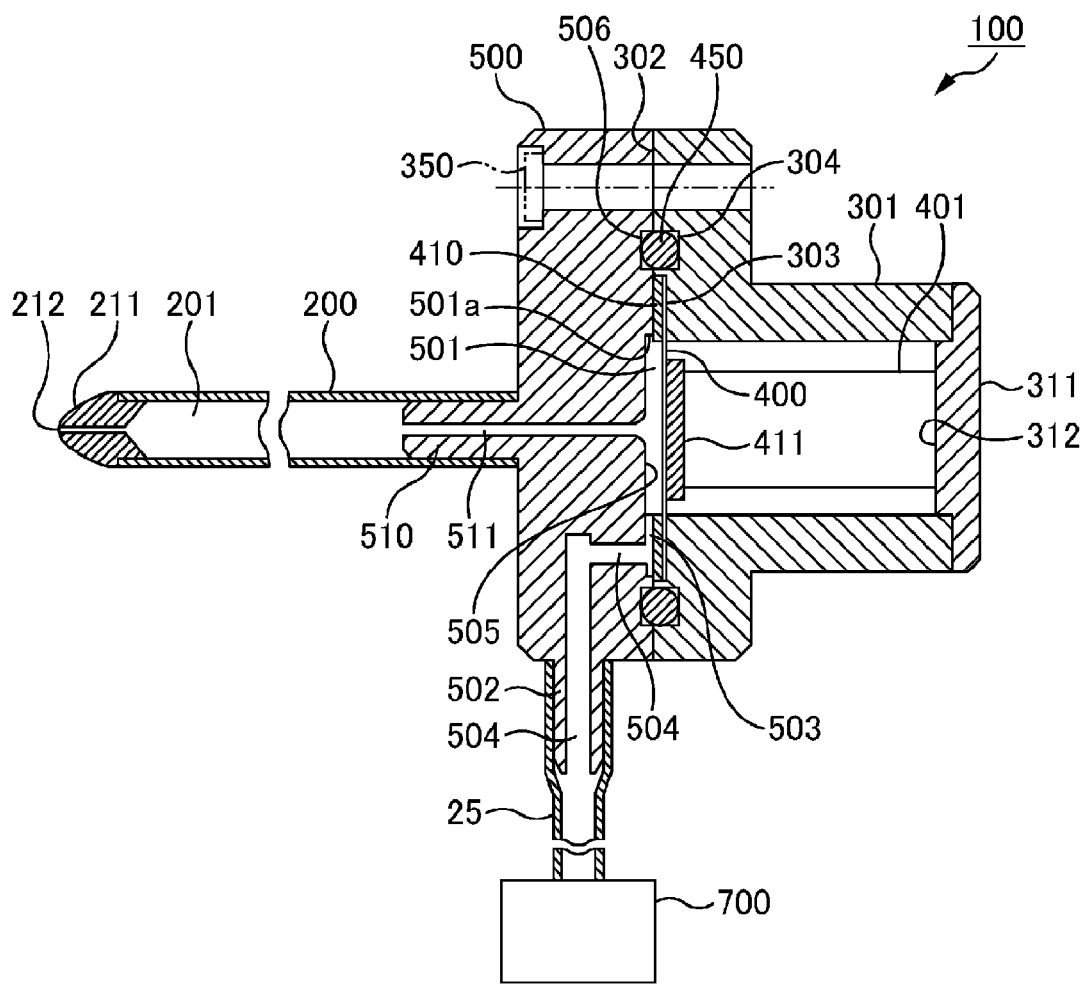
FIG. 4 is a cross-sectional view illustrating the structure of a pulsation generator according to the embodiment of the invention.

FIG. 4 is a cross-sectional view illustrating the structure of the pulsation generator 100 according to the embodiment. In FIG. 4, the pulsation generator 100 includes a pulse generation unit that generates the pulsation of the fluid, and is connected to the fluid ejection tube 200 having a connection channel 201 as a channel through which the fluid is discharged.

In the pulsation generator 100, an upper case 500 and a lower case 301 are screwed together with four fixation screws 350 (not illustrated) while the respective facing surfaces thereof are bonded to each other. The lower case 301 is a cylindrical member having a flange, and one end portion of the lower case 301 is sealed with a bottom plate 311. The piezoelectric element 401 is provided in an inner space of the lower case 301.

The piezoelectric element 401 is a stack-type piezoelectric element, and acts as an actuator. One end portion of the piezoelectric element 401 is firmly fixed to the diaphragm 400 via an upper plate 411, and the other end portion is firmly fixed to an upper surface 312 of the bottom plate 311.

The diaphragm 400 is made of a circular disc-like thin metal plate, and a circumferential edge portion of the diaphragm 400 is firmly fixed to a bottom surface of a concave portion 303 in the lower case 301 while being in close contact with the bottom surface of the concave portion 303. When drive signals are input to the piezoelectric element 401 that acts as a volume change unit, the piezoelectric element 401 changes the volume of the fluid chamber 501 via the diaphragm 400 through the extension and contraction thereof.

A reinforcement plate 410 is provided in such a manner as to be stacked on an upper surface of the diaphragm 400, and is made of a circular disc-like thin metal plate having an opening at the center thereof.

The upper case 500 has a concave portion formed in a center portion of the surface facing the lower case 301, and the fluid chamber 501 is a rotator-shaped space formed by this concave portion and the diaphragm 400 and filled with the fluid. That is, the fluid chamber 501 is a space enveloped by a sealing surface 505 and an inner side wall 501a of the concave portion of the upper case 500, and the diaphragm 400. An outlet channel 511 is drilled in an approximately center portion of the fluid chamber 501.

The outlet channel 511 passes through the outlet channel tube 510 from the fluid chamber 501 to an end portion of an outlet channel tube 510 provided in such a manner as to protrude from one end surface of the upper case 500. A connection portion between the outlet channel 511 and the sealing surface 505 of the fluid chamber 501 is smoothly rounded so as to reduce fluid resistance.

In the embodiment (refer to FIG. 4), the fluid chamber 501 described above has a substantially cylindrical shape having sealed opposite ends; however, the fluid chamber 501 may have a conical shape, a trapezoidal shape, a hemispherical shape, or the like in a side view, and the shape of the fluid chamber 501 is not limited to a cylindrical shape. For example, when the connection portion between the outlet channel 511 and the sealing surface 505 has a funnel shape, air bubbles in the fluid chamber 501 (to be described later) are easily discharged.

The fluid ejection tube 200 is connected to the outlet channel tube 510. The connection channel 201 is drilled in the fluid ejection tube 200, and the diameter of the connection channel 201 is larger than that of the outlet channel 511. In addition, the tube thickness of the fluid ejection tube 200 is formed so as to have a range of rigidity in which the fluid ejection tube 200 does not absorb pressure pulsation of the fluid.

The nozzle 211 is inserted into the tip end portion of the fluid ejection tube 200. A fluid ejection opening 212 is drilled in the nozzle 211. The diameter of the fluid ejection opening 212 is smaller than that of the connection channel 201.

An inlet channel tube (a fluid intake port) 502, into which the connection tube 25 through which the fluid is supplied from the pump 700 is inserted, is provided in such a manner as to protrude from a side surface of the upper case 500. A connection channel 504 for the inlet channel is drilled in the inlet channel tube 502. The connection channel 504 communicates with an inlet channel 503. The inlet channel 503 is formed in a groove shape in a circumferential edge portion of the sealing surface 505 of the fluid chamber 501, and communicates with the fluid chamber 501.

A packing box 304 and a packing box 506 are respectively formed in the bonded surfaces of the lower case 301 and the upper case 500 at positions separated from an outer circumferential direction of the diaphragm 400, and a ring-shaped packing 450 is mounted in a space formed by the packing boxes 304 and 506.

Here, when the upper case 500 and the lower case 301 are assembled together, the circumferential edge portion of the diaphragm 400 is in close contact with a circumferential edge portion of the reinforcement plate 410 due to the circumferential edge portion of the sealing surface 505 of the upper case 500 and the bottom surface of the concave portion 303 of the lower case 301. At this time, the packing 450 is pressed by the upper case 500 and the lowercase 301, and thereby the fluid is prevented from leaking from the fluid chamber 501.

Since the inner pressure of the fluid chamber 501 becomes a high pressure of 30 atm (3 MPa) or greater during the discharge of the fluid, the fluid may slightly leak from the respective connections between the diaphragm 400, the reinforcement plate 410, the upper case 500, and the lower case 301; however, the leakage of the fluid is prevented due to the packing 450.

As illustrated in FIG. 4, in the case where the packing 450 is provided, since the packing 450 is compressed due to the pressure of the fluid leaking from the fluid chamber 501 at a high pressure, and is strongly pressed against the respective walls of the packing boxes 304 and 506, it is possible to more reliably prevent the leakage of the fluid. For this reason, it is possible to maintain a considerable increase in the inner pressure of the fluid chamber 501 during the driving of the pulsation generator 100.

Subsequently, the inlet channel 503 formed in the upper case 500 will be described with reference to the drawings in more detail.

Figure 5:
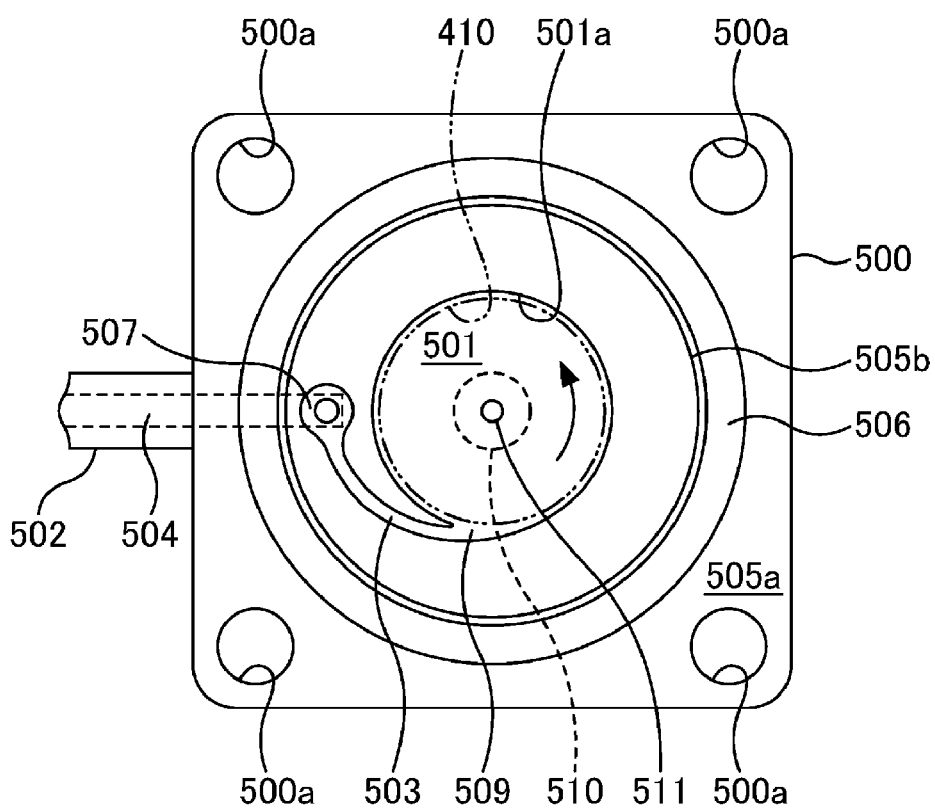
FIG. 5 is a plan view illustrating the shape of an inlet channel according to the embodiment of the invention.

FIG. 5 is a plan view illustrating the shape of the inlet channel 503, and FIG. 5 illustrates the shape of the upper case 500 when the surface of the upper case 500 bonded to the lower case 301 is seen.

In FIG. 5, the inlet channel 503 is formed in a groove shape in the circumferential edge portion of the sealing surface 505 of the upper case 500.

One end portion of the inlet channel 503 communicates with the fluid chamber 501, and the other end portion communicates with the connection channel 504. A fluid sump 507 is formed in a connection portion between the inlet channel 503 and the connection channel 504. A connection portion between the fluid sump 507 and the inlet channel 503 is smoothly rounded, and thereby fluid resistance is reduced.

The inlet channel 503 communicates with the fluid chamber 501 in a substantially tangential direction with respect to an inner circumferential side wall 501a of the fluid chamber 501. The fluid supplied from the pump 700 (refer to FIG. 1) at a predetermined pressure flows along the inner circumferential side wall 501a (in a direction illustrated by the arrow in FIG. 5), and generates a swirl flow in the fluid chamber 501. The swirl flow is pushed against the inner circumferential side wall 501a due to a centrifugal force associated with the swirling of the fluid, and air bubbles in the fluid chamber 501 are concentrated in a center portion of the swirl flow.

The air bubbles concentrated in the center portion are discharged via the outlet channel 511. For this reason, the outlet channel 511 is preferably provided in the vicinity of the center of the swirl flow, that is, in an axial center portion of a rotor shape.

As illustrated in FIG. 5, the inlet channel 503 is curved. The inlet channel 503 may communicate with the fluid chamber 501 while not being curved but being linearly formed; however, when the inlet channel 503 is curved, a channel length is increased, and a desired inertance (to be described later) is obtained in a small space.

As illustrated in FIG. 5, the reinforcement plate 410 is provided between the diaphragm 400 and the circumferential edge portion of the sealing surface 505, in which the inlet channel 503 is formed. The reinforcement plate 410 is provided so as to improve the durability of the diaphragm 400. Since a cut-out connection opening 509 is formed in a connection portion between the inlet channel 503 and the fluid chamber 501, when the diaphragm 400 is driven at a high frequency, stress may be concentrated in the vicinity of the connection opening 509, and thereby a fatigue failure may occur in the vicinity of the connection opening 509. It is possible to prevent stress from being concentrated on the diaphragm 400 by providing the reinforcement plate 410 with an opening not having a cut-out portion and being continuously formed.

Four screw holes 500a are respectively provided in outer circumferential corner portions of the upper case 500, and the upper case 500 and the lower case 301 are bonded to each other via screwing at the positions of the screw holes.

It is possible to firmly fix the reinforcement plate 410 and the diaphragm 400 in an integrally stacked state by bonding together the reinforcement plate 410 and the diaphragm 400, which is not illustrated. An adhesive method using an adhesive, a solid-state diffusion bonding method, a welding method, or the like may be used so as to firmly fix together the reinforcement plate 410 and the diaphragm 400; however, the respective bonded surfaces of the reinforcement plate 410 and the diaphragm 400 are preferably in close contact with each other.

Operation of Pulsation Generator

Subsequently, an operation of the pulsation generator 100 according to the embodiment will be described with reference to FIGS. 1 to 5. The pulsation generator 100 according to the embodiment discharges the fluid due to a difference between an inertance L1 (may be referred to as a combined inertance L1) of the inlet channel 503 side and an inertance L2 (may be referred to as a combined inertance L2) of the outlet channel 511 side.

Inertance

First, the inertance will be described.

An inertance L is expressed by $L=\rho \times h/S$, and here, $\rho$ is the density of a fluid, S is the cross-sectional area of a channel, and h is a channel length. When $\Delta P$ is a differential pressure of the channel, and Q is a flow rate of the fluid flowing through the channel, it is possible to deduce a relationship $\Delta P=L \times dQ/dt$ by modifying an equation of motion in the channel using the inertance L.

That is, the inertance L indicates a degree of influence on a change in flow rate with time, and a change in flow rate with time decreases to the extent that the inertance L is large, and a change in flow rate with time increases to the extent that the inertance L is small.

Similar to a parallel connection or a series connection of inductances in an electric circuit, it is possible to calculate a combined inertance with respect to a parallel connection of a plurality of channels or a series connection of a plurality of channels having different shapes by combining an inertance of each of the channels.

Since the diameter of the connection channel 504 is set to be larger much than that of the inlet channel 503, the inertance L1 of the inlet channel 503 side can be calculated from a boundary of the inlet channel 503. At this time, since the connection tube 25 that connects the pump 700 and the inlet channel 503 is flexible, the connection tube 25 may not be taken into consideration in calculating the inertance L1.

Since the diameter of the connection channel 201 is much larger than that of the outlet channel 511, and the tube (tube wall) thickness of the fluid ejection tube 200 is thin, the connection channel 201 has a negligible influence on the inertance L2 of the outlet channel 511 side. Accordingly, the inertance L2 of the outlet channel 511 side may be replaced with an inertance of the outlet channel 511.

The rigidity of the tube wall thickness of the fluid ejection tube 200 is sufficient to propagate the pressure of the fluid.

In the embodiment, a channel length and a cross-sectional area of the inlet channel 503 and a channel length and a cross-sectional area of the outlet channel 511 are set in such a manner that the inertance L1 of the inlet channel 503 side is greater than the inertance L2 of the outlet channel 511 side.

Ejection of Fluid

Subsequently, an operation of the pulsation generator 100 will be described.

The pump 700 supplies the fluid to the inlet channel 503 at a predetermined pressure. As a result, when the piezoelectric element 401 is not operated, the fluid flows into the fluid chamber 501 due to a difference between a discharge force of the pump 700 and a fluid resistance value for the entirety of the inlet channel 503 side.

Here, in a case where the inertance L1 of the inlet channel 503 side and the inertance L2 of the outlet channel 511 side are considerably large, when a drive signal is input to the piezoelectric element 401, and the piezoelectric element 401 extends rapidly, the inner pressure of the fluid chamber 501 increases rapidly, and reaches several tens of atmosphere.

Since the inner pressure of the fluid chamber 501 is much larger than the pressure applied to the inlet channel 503 by the pump 700, the flow of the fluid from the inlet channel 503 to the fluid chamber 501 decreases due to the pressure, and the flow of the fluid out of the outlet channel 511 increases.

Since the inertance L1 of the inlet channel 503 is larger than the inertance L2 of the outlet channel 511, an increase in a flow rate of the fluid discharged from the outlet channel 511 is larger than a decrease in a flow rate of the fluid flowing from the inlet channel 503 into the fluid chamber 501. Accordingly, the fluid is discharged in the form of a pulsed flow to the connection channel 201, that is, a pulsed flow occurs. Discharge pressure pulsation propagates in the fluid ejection tube 200, and the fluid is ejected via the fluid ejection opening 212 of the nozzle 211 at the tip end.

Here, since the diameter of the fluid ejection opening 212 of the nozzle 211 is smaller than that of the outlet channel 511, a pulsed flow of the fluid is ejected as droplets at a higher pressure and speed.

In contrast, immediately after a pressure increase, the inner pressure of the fluid chamber 501 becomes negative due to interaction between a decrease in the amount of inflow of the fluid from the inlet channel 503 and an increase in the amount of outflow of the fluid from the outlet channel 511. As a result, after a predetermined amount of time has elapsed, due to both of the pressure of the pump 700 and the negative inner pressure of the fluid chamber 501, the fluid flows from the inlet channel 503 into the fluid chamber 501 again at the same speed as that before the operation of the piezoelectric element 401.

When the piezoelectric element 401 extends after the outflow of the fluid from the inlet channel 503 is restored, it is possible to continuously eject the fluid in the form of a pulsed flow via the nozzle 211.

Discharge of Air Bubbles

Subsequently, an operation of discharging air bubbles from the fluid chamber 501 will be described.

As described above, the inlet channel 503 communicates with the fluid chamber 501 via a path that approaches the fluid chamber 501 while swirling around the fluid chamber 501. The outlet channel 511 is provided in the vicinity of a rotational axis of a substantially rotor-shaped fluid chamber 501.

For this reason, the fluid flowing from the inlet channel 503 into the fluid chamber 501 swirls along the inner circumferential side wall 501a of the fluid chamber 501. The fluid is pushed against the inner circumferential side wall 501a of the fluid chamber 501 due to a centrifugal force, and air bubbles contained in the fluid are concentrated in the center portion of the fluid chamber 501, and are discharged via the outlet channel 511.

Accordingly, even when a small amount of the volume of the fluid chamber 501 is changed in association with the operation of the piezoelectric element 401, it is possible to obtain a sufficient pressure increase while a pressure pulsation is not adversely affected.

In the embodiment, since the pump 700 supplies the fluid to the inlet channel 503 at a predetermined pressure, even when the driving of the pulsation generator 100 is stopped, the fluid is supplied to the inlet channel 503 and the fluid chamber 501. Accordingly, it is possible to start an initial operation without an aid of a prime operation.

Since the fluid is ejected via the fluid ejection opening 212 having a diameter smaller than that of the outlet channel 511, an inner fluid pressure is increased higher than that of the outlet channel 511, and thereby it is possible to eject the fluid at a high speed.

Since the rigidity of the fluid ejection tube 200 is sufficient to transmit a pulsation of the fluid from the fluid chamber 501 to the fluid ejection opening 212, it is possible to eject the fluid in the form of a desired pulsed flow without disturbing pressure propagation of the fluid from the pulsation generator 100.

Since the inertance of the inlet channel 503 is set to be larger than that of the outlet channel 511, an increase in the amount of outflow of the fluid from the outlet channel 511 is larger than a decrease in the amount of flow of the fluid from the inlet channel 503 into the fluid chamber 501, and it is possible to discharge the fluid into the fluid ejection tube 200 in the form of a pulsed flow. Accordingly, a check valve is not required to be provided in the inlet channel 503, it is possible to simplify the structure of the pulsation generator 100, it is easy to clean the inside of the pulsation generator 100, and it is possible to remove a potential durability problem associated with the use of the check valve.

Since the respective inertances of both of the inlet channel 503 and the outlet channel 511 are set to be considerably large, it is possible to rapidly increase the inner pressure of the fluid chamber 501 by rapidly reducing the volume of the fluid chamber 501.

Since the piezoelectric element 401 as a volume change unit and the diaphragm 400 are configured so as to generate a pulsation, it is possible to simplify the structure of the pulsation generator 100 and to reduce the size of the pulsation generator 100 in association therewith. It is possible to set the maximum frequency of a change in the volume of the fluid chamber 501 to a high frequency of 1 KHz or greater, and the pulsation generator 100 is optimized to eject a pulsed flow of the fluid at a high speed.

In the pulsation generator 100, since the inlet channel 503 generates a swirl flow of the fluid in the fluid chamber 501, the fluid in the fluid chamber 501 is pushed in an outer circumferential direction of the fluid chamber 501 due to a centrifugal force, air bubbles contained in the fluid are concentrated in the center portion of the swirl flow, that is, in the vicinity of the axis of the substantially rotor shape, and thereby it is possible to discharge the air bubbles via the outlet channel 511 provided in the vicinity of the axis of the substantially rotor shape. For this reason, it is possible to prevent a decrease in pressure amplitude associated with the stagnation of air bubbles in the fluid chamber 501, and it is possible to continuously and stably drive the pulsation generator 100.

Since the inlet channel 503 is formed in such a manner as to communicate with the fluid chamber 501 via the path that approaches the fluid chamber 501 while swirling around the fluid chamber 501, it is possible to generate a swirl flow without adopting a structure dedicated for swirling the fluid in the fluid chamber 501.

Since the groove-shaped inlet channel 503 is formed in the outer circumferential edge portion of the sealing surface 505 of the fluid chamber 501, it is possible to form the inlet channel 503 as a swirl flow generation unit without increasing the number of components.

Since the reinforcement plate 410 is provided on the upper surface of the diaphragm 400, the diaphragm 400 is driven with respect to an outer circumference of the opening of the reinforcement plate 410 as a fulcrum, and thereby the concentration of stress is unlikely to occur, and it is possible to improve the durability of the diaphragm 400.

When corners of the surface of the reinforcement plate 410 bonded to the diaphragm 400 are rounded, it is possible to further reduce the concentration of stress on the diaphragm 400.

When the reinforcement plate 410 and the diaphragm 400 are firmly and integrally fixed together while being stacked on each other, it is possible to improve the assemblability of the pulsation generator 100, and it is possible to reinforce the outer circumferential edge portion of the diaphragm 400.

Since the fluid sump 507 for the stagnation of the fluid is provided in the connection portion between the connection channel 504 on an inlet side for supplying the fluid from the pump 700 and the inlet channel 503, it is possible to prevent the inertance of the connection channel 504 from affecting the inlet channel 503.

In the respective bonded surfaces of the lower case 301 and the upper case 500, the ring-shaped packing 450 is provided at the position separated from the outer circumferential direction of the diaphragm 400, and thereby it is possible to prevent the leakage of the fluid from the fluid chamber 501, and to prevent a decrease in the inner pressure of the fluid chamber 501.

Detection of Blocking of Connection Tube

As described above, in the fluid ejection device 1 according to the embodiment, when the practitioner inputs an ON signal of the pulsation generator start-up switch 625 to the drive control unit 600 by operating the pulsation generator start-up switch 625, the pump control unit 710 moves the slider 720 at the predetermined speed in the push-in direction, and thereby the fluid accommodation portion 765 is pressed, and the fluid flows to the connection path via the opening 764 of the fluid accommodation portion 765. Also, in the priming process, the pump control unit 710 moves the slider 720 at the predetermined speed in the push-in direction, and thereby the fluid accommodation portion 765 is pressed, and the fluid flows to the connection path via the opening 764 of the fluid accommodation portion 765.

Accordingly, as described above, when the pump control unit 710 presses the fluid accommodation portion 765, and in a case where the connection path is blocked due to the intrusion of foreign matter into the connection tube 25, the clogging of a filter (not illustrated) provided on the connection path, the clogging of the nozzle 211 of the pulsation generator 100, the misconnection of the connection tube 25, the missetting of an orientation of the three way stopcock 26, or the like, an inner pressure in the fluid accommodation portion 765 and the connection piping may become an unexpected high pressure.

The fluid ejection device 1 according to the embodiment can detect the blocking of the connection path (the connection piping) between the pump 700 and the pulsation generator 100.

Figure 6:
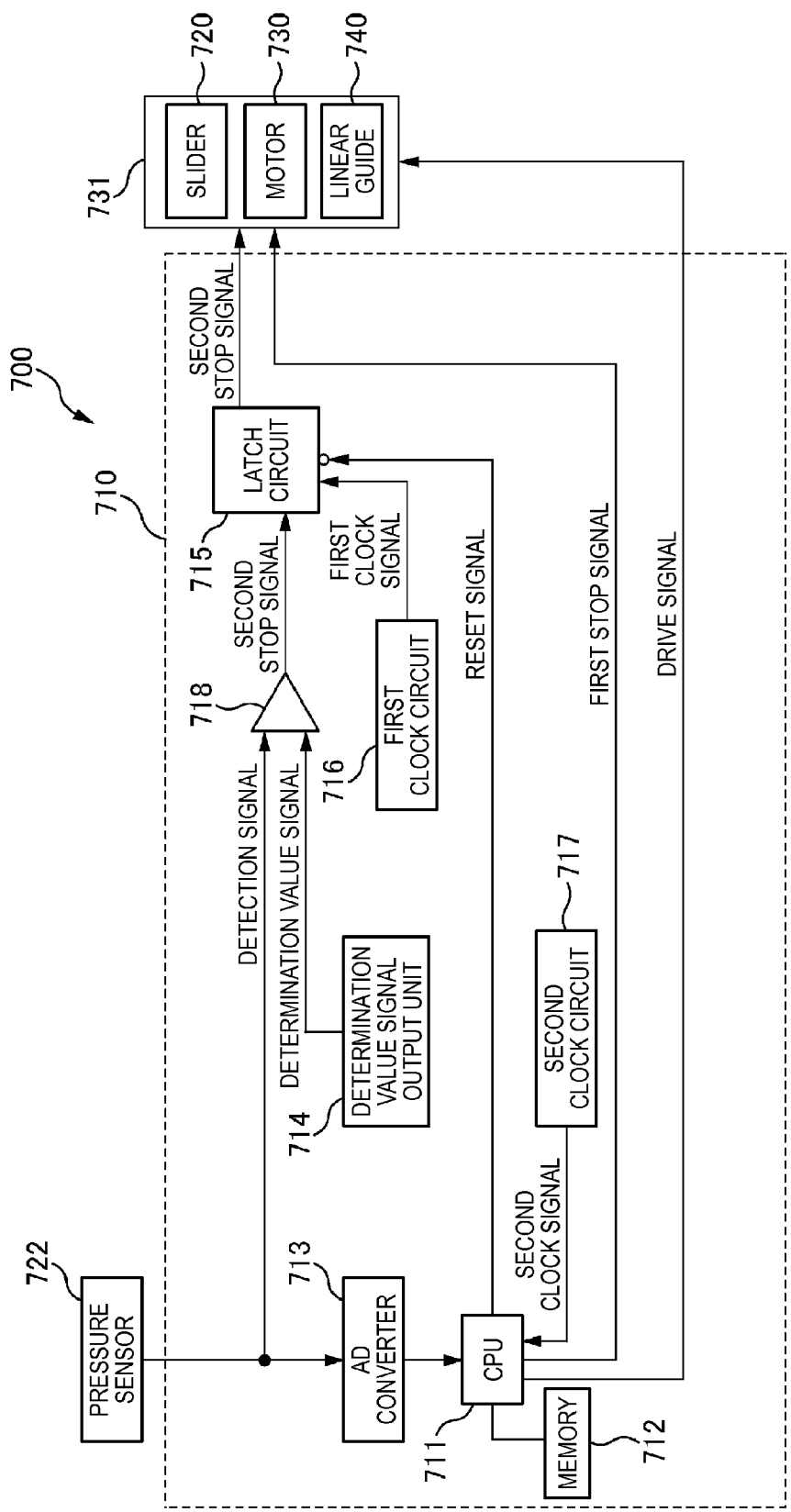
FIG. 6 is a block diagram illustrating the configuration of a pump control unit according to the embodiment of the invention.

In the embodiment, a process of detecting the blocking of the connection path performed by the fluid ejection device 1 will be described in detail with reference to FIGS. 6 to 8.

First, the configuration of the pump control unit (the press control unit) 710 will be described with reference to FIG. 6.

The pump control unit 710 is configured to have a central processing unit (CPU) (a processor) 711, a memory 712, an analog/digital (AD) converter 713, a digital/analog (DA) converter (a determination value signal output circuit) 714, a latch circuit 715, a first clock circuit 716, a second clock circuit 717, and a comparator 718.

The pump control unit 710 takes a detection signal from the pressure sensor 722, the detection signal corresponding to the pressure when the fluid pressing unit 731 presses the fluid accommodation portion 765 of the fluid container 760, and the pump control unit 710 controls the fluid pressing unit 731. For example, when the pump control unit 710 receives an ON signal of the slider set switch 781, the pump control unit 710 controls the pressure to become the target pressure value by outputting a predetermined drive signal to the fluid pressing unit 731 and driving the motor 730.

When the pressure is higher than a predetermined determination value, the pump control unit 710 outputs a first stop signal or a second stop signal (to be described later) to the fluid pressing unit 731, and stops the pressing of the fluid accommodation portion 765. The fluid pressing unit 731 is configured to have the slider 720, the motor 730, and the linear guide 740.

The CPU 711 controls the entirety of the pump control unit 710, and realizes various functions of the embodiment by executing a program stored in the memory 712 and coded to perform various operations.

The memory 712 stores various pieces of data other than the program. For example, the memory 712 stores determination value level data indicative of a level equivalent to the predetermined determination values (containing the first determination value and the second determination value which will be described later).

The AD converter 713 receives a detection signal output from the pressure sensor 722, and outputs data indicative of the level of the detection signal. Specifically, the pressure sensor 722 detects the pressure when the slider 720 presses the fluid accommodation portion 765, and outputs a level (for example, a voltage) of a detection signal corresponding to the pressure. The AD converter 713 outputs detected level data (for example, a voltage value) indicative of the level of the detection signal output from the pressure sensor 722.

The CPU 711 takes the detected level data output from the AD converter 713, and compares the detected level data with the determination value level data stored in the memory 712. When the detected level data is the determination value level data or greater, the CPU 711 outputs the first stop signal to the fluid pressing unit 731 so as to stop the fluid pressing unit 731 from pressing the fluid accommodation portion 765.

The fluid pressing unit 731 stops the driving of the motor 730 immediately after acquiring the first stop signal.

In this manner, the fluid ejection device 1 according to the embodiment can detect the blocking of the connection piping, and prevent occurrences of various malfunctions associated with the blocking. Accordingly, it is possible to improve the safety and the reliability of the fluid ejection device 1.

The pump control unit 710 according to the embodiment has the comparator circuit 718.

A detection signal is input to one input terminal of the comparator circuit 718 from the pressure sensor 722. A determination value signal is input to the other terminal of the comparator circuit 718 from a determination value signal output unit 714. The determination value signal is a signal having a level equivalent to the determination value. For example, the determination value signal output unit 714 can be configured to have a constant voltage power supply that outputs a voltage equivalent to the determination value.

The comparator circuit 718 compares the level of the detection signal from the pressure sensor 722 and the level of the determination value signal, and when the level of the detection signal is greater than or equal to the level of the determination value signal, the comparator circuit 718 outputs the second stop signal to the latch circuit 715 so as to stop the fluid pressing unit 731 from pressing the fluid accommodation portion 765.

The latch circuit 715 takes the second stop signal from the comparator circuit 718, and outputs the second stop signal to the fluid pressing unit 731 at a time synchronous with a predetermined frequency of a first clock signal from the first clock circuit 716.

For this reason, until the second stop signal is output from the latch circuit 715 after the second stop signal is output from the comparator circuit 718, it is possible to generate a constant time delay or longer determined corresponding to the frequency of the first clock signal.

The second stop signal from the latch circuit 715 is input to the fluid pressing unit 731. The fluid pressing unit 731 stops the driving of the motor 730 immediately after receiving the second stop signal.

In this manner, the fluid ejection device 1 according to the embodiment can detect the blocking of the connection piping without the CPU 711 intervening therewith. For this reason, for example, even when a failure of the CPU 711 occurs, it is possible to prevent occurrences of various malfunctions associated with the blocking of the connection piping. Accordingly, it is possible to further improve the safety or the reliability of the fluid ejection device 1.

The CPU 711 operates synchronously with a second clock signal from the second clock circuit 717. The frequency of the second clock signal is greater (for example, several times to several hundred of times or greater) than that of the first clock signal from the first clock circuit 716.

The CPU 711 repeatedly outputs a reset signal to the latch circuit 715 at a time synchronous with the second clock signal.

For this reason, when the CPU 711 operates normally, the latch circuit 715 is repeatedly reset by the CPU 711 at the time synchronous with the second clock signal. Accordingly, even when the second stop signal is input to the latch circuit 715 from the comparator circuit 718, the latch circuit 715 is reset before the second stop signal is output from the latch circuit 715.

Accordingly, for example, it is possible to prevent the comparator circuit 718 from outputting the second stop signal, and the fluid pressing unit 731 from erroneously being stopped in a case where the level of a detection signal from the pressure sensor 722 increases temporarily due to noise or the like. As a result, it is possible to improve the reliability of the fluid ejection device 1.

When the first stop signal or the second stop signal is output to the fluid pressing unit 731 from the pump control unit 710, the fluid pressing unit 731 stops the pressing of the fluid accommodation portion 765; however, for example, the pressing of the fluid accommodation portion 765 may be stopped by shutting off electrical power used when the fluid pressing unit 731 presses the fluid accommodation portion 765 when the first stop signal or the second stop signal is input to the fluid pressing unit 731.

In this configuration, since it is possible to shut off electrical power used when the fluid pressing unit 731 presses the fluid accommodation portion 765, it is possible to reliably stop the pressing of the fluid accommodation portion 765.

When the pump control unit 710 detects the blocking of the connection piping, and outputs the first stop signal, the pump control unit 710 may transmit a command for stopping the driving of the piezoelectric element 401 of the pulsation generator 100 to the drive control unit 600, and stop the pulsation generator 100 from ejecting the fluid in a pulsed manner.

In this manner, since it is possible to prevent residual pressure in the connection tube from causing the pulsation generator 100 to continuously eject the fluid at a high pressure, it is possible to further improve the safety of the fluid ejection device 1.

When the pump control unit 710 detects the blocking of the connection piping, and outputs the first stop signal, the pump control unit 710 may output a predetermined alarm. For example, the pump control unit 710 outputs a voice message that an inner pressure in the connection piping is greater than the determination value. Alternatively, the pump control unit 710 may turn on a predetermined alarm lamp (not illustrated).

In this manner, it is possible to promptly notify an operator such as a practitioner that the connection piping is blocked, and it is possible to further improve the safety of the fluid ejection device 1.

When pressure indicated by a detection signal from the pressure sensor 722 is the determination value or greater, the pump control unit 710 can stop the fluid pressing unit 731 from pressing the fluid accommodation portion 765, and reduce the inner pressure of the fluid accommodation portion 765.

In this case, for example, when the fluid pressing unit 731 receives the first stop signal or the second stop signal, the fluid pressing unit 731 stops the movement of the slider 720 in the push-in direction, and then moves the slider 720 in the opposite direction of the push-in direction. Accordingly, since the slider 720 and the plunger 762 move in the opposite direction of the push-in direction, the inner pressure of the fluid accommodation portion 765 decreases.

In this manner, since it is possible to rapidly release a high pressure originating from the blocking of the connection piping, and to easily reduce the high pressure to a safe level, it is possible to further improve the safety of the fluid ejection device 1. In addition, thereafter, it is possible to more safely perform maintenance or the like.

Subsequently, a flow of the process of detecting the blocking of the connection piping according to the embodiment will be described with reference to FIGS. 7 and 8.

Figure 7:
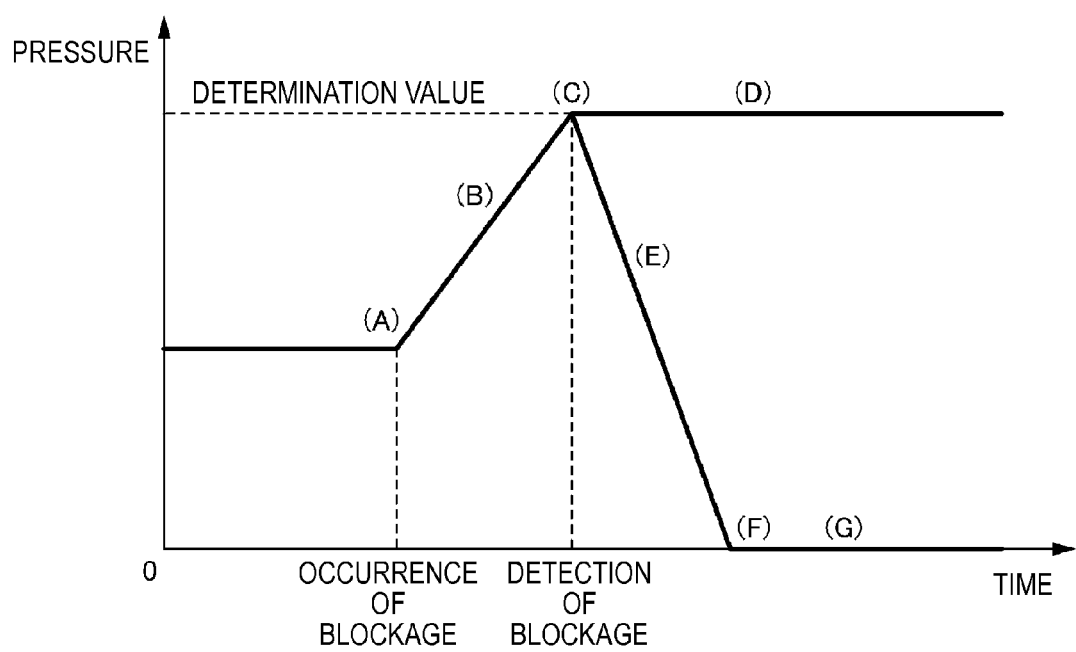
FIG. 7 is a graph illustrating a transition in an inner pressure in a connection path according to the embodiment of the invention.

FIG. 7 is a graph illustrating a change over time in the inner pressure of the fluid accommodation portion 765 detected by the pressure sensor 722 when the pump control unit 710 controls the slider 720 to move at the predetermined speed in the push-in direction.

(A) in FIG. 7 indicates a time when the connection piping is blocked for unknown reasons.

As illustrated by (B) in FIG. 7, the inner pressure of the fluid accommodation portion 765 increases over time.

When the inner pressure of the fluid accommodation portion 765 reaches the determination value ((C) in FIG. 7), as described above, the pump control unit 710 outputs the first stop signal or the second stop signal to the fluid pressing unit 731, and stops the fluid pressing unit 731 pressing the fluid accommodation portion 765.

Accordingly, as illustrated in (D) in FIG. 7, it is possible to stop an increase in the inner pressure of the fluid accommodation portion 765.

Alternatively, when the pump control unit 710 controls the fluid pressing unit 731 to reduce the inner pressure of the fluid accommodation portion 765, as illustrated by (E) and (G) in FIG. 7, it is possible to reduce the inner pressure of the fluid accommodation portion 765 and to decrease the inner pressure to approximately zero.

Figure 8:
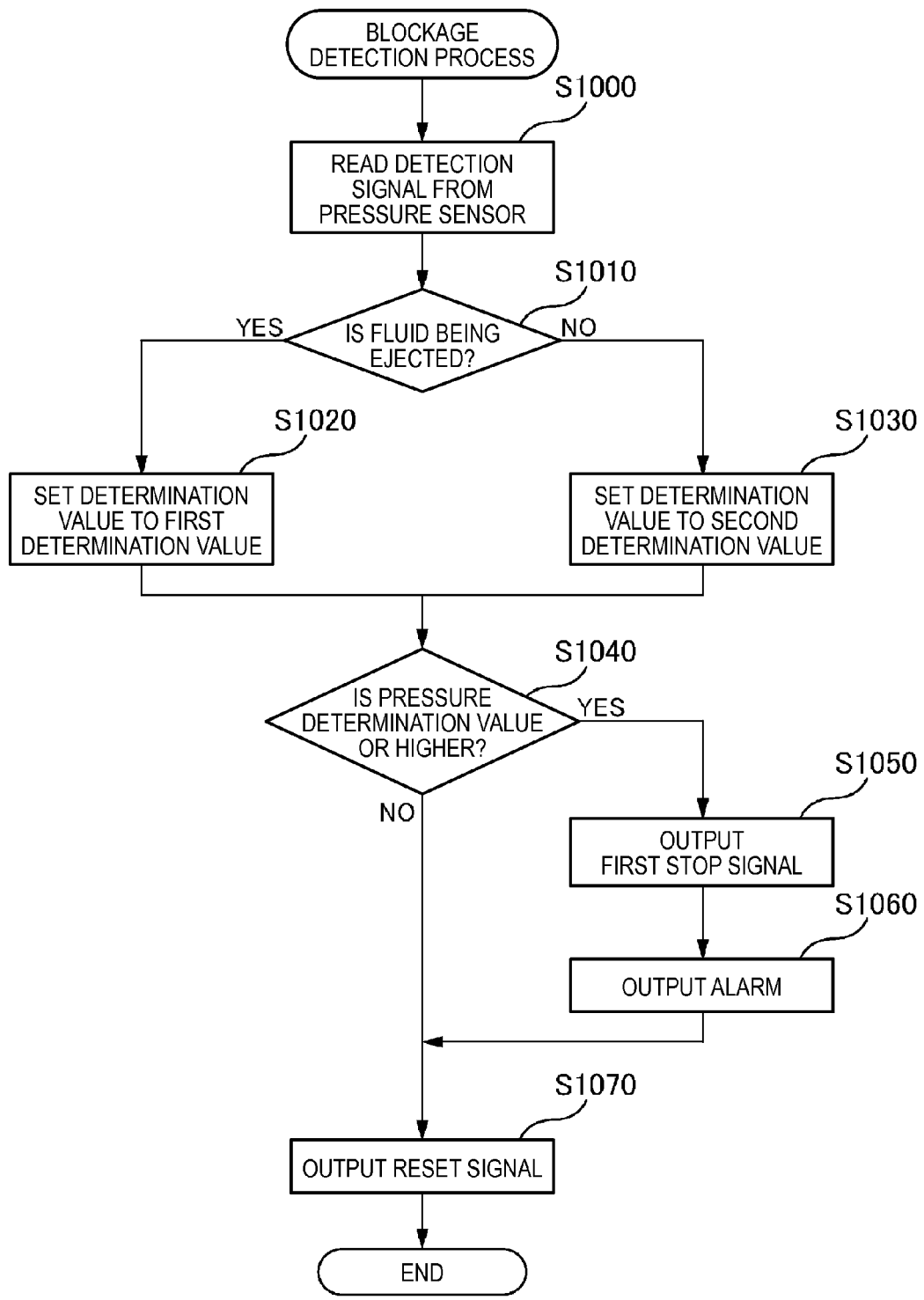
FIG. 8 is a flowchart illustrating a flow of a process performed by the pump control unit according to the embodiment of the invention.

FIG. 8 is a flowchart illustrating a flow of the process performed by the CPU 711.

For example, the CPU 711 executes the process illustrated in FIG. 8 every 20 milliseconds at a time synchronous with the second clock signal.

First, the CPU 711 acquires detected level data (a voltage value) from the AD converter 713, the detected level data being indicative of the level (voltage) of the detection signal from the pressure sensor 722 (S1000).

Subsequently, the CPU 711 determines whether the fluid is being ejected from the pulsation generator 100 (whether the piezoelectric element 401 is being driven) (S1010). The CPU 711 determines whether the fluid is being ejected by acquiring information from the drive control unit 600 by communication via the communication cable 640, the information being indicative of whether the pulsation generator start-up switch 625 is turned on or off.

When the fluid is being ejected, the CPU 711 reads the determination value level data (voltage value) from the memory 712, the determination value level data being indicative of a level (voltage) equivalent to the first determination value (a pressure) stored in the memory 712 (S1020). When the fluid is not being ejected, the CPU 711 reads determination value level data (a voltage value) from the memory 712, the determination value level data being indicative of a level (a voltage) equivalent to the second determination value (a pressure) stored in the memory 712 (S1030).

The first determination value is a value determined corresponding to the target pressure value when the fluid pressing unit 731 presses the fluid accommodation portion 765. For example, the first determination value can be a value obtained by adding a predetermined value to the target pressure value, or a value obtained by increasing the target pressure value by a predetermined ratio.

As such, it is possible to properly detect the blocking of the connection piping corresponding to the target pressure value which is changing according to circumstances from moment to moment by detecting the blocking of the connection piping using the determination value determined corresponding to the target pressure value.

The second determination value is a predetermined fixed value. As such in the priming process, the fluid may flow to the pulsation generator 100 by moving the slider 720 in the push-in direction without the driving of the piezoelectric element 401. In this case, since there is no target pressure value set, the blocking of the connection piping is detected by using the second determination value that is a fixed value.

As such, in the fluid ejection device 1 according to the embodiment, when the fluid is being ejected from the pulsation generator 100, it is possible to precisely detect the blocking of the connection tube by using the determination value (the first determination value) determined corresponding to the target pressure value when the fluid pressing unit 731 presses the fluid accommodation portion 765, and when the fluid is not being ejected, in which there is no target pressure value set, it is possible to detect the blocking of the connection piping by using the determination value (the second determination value) that is the predetermined fixed value.

Subsequently, the CPU 711 compares the detected level data acquired from the AD converter with the determination value level data read from the memory, and determines whether the pressure indicated by the detection signal from the pressure sensor 722 is the determination value or higher (S1040).

When the pressure indicated by the detection signal from the pressure sensor 722 is not the determination value or higher, the CPU 711 outputs a reset signal to the latch circuit 715, and ends the process (S1070).

In contrast, when the pressure indicated by the detection signal from the pressure sensor 722 is the determination value or higher, the CPU 711 outputs the first stop signal (S1050), and outputs the predetermined alarm (S1060). Then, the CPU 711 outputs a reset signal to the latch circuit 715, and ends the process (S1070).

The fluid ejection device 1 according to the embodiment has been described, and in the fluid ejection device 1 according to the embodiment, it is possible to detect the blocking of the connection piping that acts as the fluid channel between the pump 700 and the pulsation generator 100, and to improve the safety or the reliability of the fluid ejection device 1.

The embodiment is presented so as to help the understanding of the invention, and does not limit the interpretation of the invention. Modifications and improvements can be made to the invention insofar as the modifications and the improvements do not depart from the spirit of the invention, and the equivalents are also included in the invention.

What is claimed is:

1. A fluid ejection device comprising:
   a fluid container that has a fluid accommodation portion for accommodating a fluid, and a fluid outlet formed in the fluid accommodation portion;
   a fluid pressing unit that presses the fluid accommodation portion to cause the fluid to flow out of the fluid outlet;
   connection piping, one end of which is connected to the fluid outlet;
   a fluid ejection unit that has a fluid intake port connected to the other end of the connection piping, and ejects in a pulsed manner the fluid taken in via the fluid intake port;
   a pressure detection unit that detects a pressure of the fluid accommodation portion when the fluid pressing unit presses the fluid accommodation portion, and outputs a level of a detection signal corresponding to the pressure; and
   a press control unit that stops the fluid pressing unit from pressing the fluid accommodation portion when the pressure indicated by the detection signal is a predetermined determination value or higher,
   wherein when the pressure indicated by the detection signal is the predetermined determination value or higher, the press control unit stops the fluid pressing unit from pressing the fluid accommodation portion, and stops the fluid ejection unit from ejecting the fluid in a pulsed manner.

2. The fluid ejection device according to claim 1,
wherein the press control unit stops the pressing of the fluid accommodation portion by shutting off electrical power used when the fluid pressing unit presses the fluid accommodation portion.

3. The fluid ejection device according to claim 1,
wherein the predetermined determination value is a value determined corresponding to a target pressure value when the fluid pressing unit presses the fluid accommodation portion.

4. The fluid ejection device according to claim 1, further comprising:
an operation input unit that receives an operation input to enable or disable the ejection of the fluid from the fluid ejection unit; and
a drive control unit that drives a pressurization element provided in the fluid ejection unit so as to apply a pulsed pressure to the fluid taken in via the fluid intake port when the drive control unit receives an operation input to enable the ejection of the fluid, and stops the driving of the pressurization element when the drive control unit receives an operation input to disable the ejection of the fluid,
wherein when the pressurization element is being driven, the press control unit compares the pressure indicated by the detection signal with a first determination value determined corresponding to the target pressure value when the fluid pressing unit presses the fluid accommodation portion, and when the pressurization element is not being driven, the press control unit compares the pressure indicated by the detection signal with a second determination value that is a predetermined fixed value.

5. The fluid ejection device according to claim 1,
wherein when the pressure indicated by the detection signal is the determination value or higher, the press control unit outputs an alarm to notify that the pressure is the determination value or higher.

6. The fluid ejection device according to claim 1,
wherein when the pressure indicated by the detection signal is the determination value or higher, the press control unit stops the fluid pressing unit from pressing the fluid accommodation portion, and reduces an inner pressure of the fluid accommodation portion.

7. The fluid ejection device according to claim 1,
wherein the press control unit includes:
an AD converter that receives the detection signal from the pressure detection unit, and outputs detected level data indicative of the level of the detection signal;
a memory that stores determination value level data indicative of a level equivalent to the determination value;
a processor that outputs a first stop signal for stopping the fluid pressing unit from pressing the fluid accommodation portion to the fluid pressing unit when the detected level data from the AD converter is compared with the determination value level data stored in the memory, and the detected level data is the determination value level data or greater;
a determination value signal output circuit that outputs a level of a determination value signal equivalent to the determination value;
a comparator circuit that outputs a second stop signal for stopping the fluid pressing unit from pressing the fluid accommodation portion when the detection signal from the pressure detection unit and the determination value signal are input to the comparator circuit, the level of the detection signal is compared with the level of the determination value signal, and the level of the detection signal is the level of the determination value signal or higher; and
a latch circuit that receives the second stop signal from the comparator circuit, and outputs the second stop signal to the fluid pressing unit at a time synchronous with a predetermined frequency of a clock signal,
wherein when the first stop signal or the second stop signal is input, the fluid pressing unit stops the pressing of the fluid accommodation portion, and
wherein the processor outputs a reset signal to the latch circuit so as to reset the latch circuit before the latch circuit outputs the second stop signal synchronously with the clock signal.

8. The fluid ejection device according to claim 1, wherein the fluid pressing unit decreases an inner pressure of the fluid accommodation portion when the pressure indicated by the detection signal is the predetermined determination value or higher.

9. A fluid ejection device comprising:
a fluid container that has a fluid accommodation portion for accommodating a fluid, and a fluid outlet formed in the fluid accommodation portion;
a fluid pressing unit that presses the fluid accommodation portion to cause the fluid to flow out of the fluid outlet;
connection piping, one end of which is connected to the fluid outlet;
a fluid ejection unit that has a fluid intake port connected to the other end of the connection piping, and ejects in a pulsed manner the fluid taken in via the fluid intake port;
a pressure detection unit that detects a pressure of the fluid accommodation portion when the fluid pressing unit presses the fluid accommodation portion, and outputs a level of a detection signal corresponding to the pressure; and
a press control unit that stops the fluid pressing unit from pressing the fluid accommodation portion when the pressure indicated by the detection signal is a predetermined determination value or higher,
wherein when the pressure indicated by the detection signal is the determination value or higher, the press control unit outputs an alarm to notify that the pressure is the determination value or higher.

10. A fluid ejection device comprising:
a fluid container that has a fluid accommodation portion for accommodating a fluid, and a fluid outlet formed in the fluid accommodation portion;
a fluid pressing unit that presses the fluid accommodation portion to cause the fluid to flow out of the fluid outlet;
connection piping, one end of which is connected to the fluid outlet;
a fluid ejection unit that has a fluid intake port connected to the other end of the connection piping, and ejects in a pulsed manner the fluid taken in via the fluid intake port;
a pressure detection unit that detects a pressure of the fluid accommodation portion when the fluid pressing unit presses the fluid accommodation portion, and outputs a level of a detection signal corresponding to the pressure; and
a press control unit that stops the fluid pressing unit from pressing the fluid accommodation portion when the pressure indicated by the detection signal is a predetermined determination value or higher,
wherein the press control unit includes:
an AD converter that receives the detection signal from the pressure detection unit, and outputs detected level data indicative of the level of the detection signal;

a memory that stores determination value level data indicative of a level equivalent to the determination value;

a processor that outputs a first stop signal for stopping the fluid pressing unit from pressing the fluid accommodation portion to the fluid pressing unit when the detected level data from the AD converter is compared with the determination value level data stored in the memory, and the detected level data is the determination value level data or greater;

a determination value signal output circuit that outputs a level of a determination value signal equivalent to the determination value;

a comparator circuit that outputs a second stop signal for stopping the fluid pressing unit from pressing the fluid accommodation portion when the detection signal from the pressure detection unit and the determination value signal are input to the comparator circuit, the level of the detection signal is compared with the level of the determination value signal, and the level of the detection signal is the level of the determination value signal or higher; and a latch circuit that receives the second stop signal from the comparator circuit, and outputs the second stop signal to the fluid pressing unit at a time synchronous with a predetermined frequency of a clock signal, wherein when the first stop signal or the second stop signal is input, the fluid pressing unit stops the pressing of the fluid accommodation portion, and wherein the processor outputs a reset signal to the latch circuit so as to reset the latch circuit before the latch circuit outputs the second stop signal synchronously with the clock signal.

* * * * *